United States Patent [19]

Simmons

[11] Patent Number: 5,441,723
[45] Date of Patent: Aug. 15, 1995

[54] NON-TOXIC HYPOCOMPATIBLE BIODEGRADABLE GERMICIDE

[75] Inventor: Paul L. Simmons, Gulfport, Fla.

[73] Assignee: Rost, Incorporated, St. Petersburg, Fla.

[21] Appl. No.: 92,556

[22] Filed: Jul. 16, 1993

Related U.S. Application Data

[63] Continuation-in-part of Ser. No. 846,249, Feb. 24, 1992, abandoned, which is a continuation-in-part of Ser. No. 642,709, Jan. 17, 1991, Pat. No. 5,145,663, which is a continuation of Ser. No. 304,312, Jan. 31, 1989, abandoned.

[51] Int. Cl.$^6$ .......................... A61L 2/18; A61L 9/14; A61K 31/045; A61K 9/12
[52] U.S. Cl. .......................... 424/47; 424/45; 424/76.80; 514/975; 422/28
[58] Field of Search ............ 424/47, 45, 76.8, 76.2, 424/76.1; 422/28; 514/975

[56] References Cited

U.S. PATENT DOCUMENTS 4,511,486 4/1985 Shah ........................ 424/45

OTHER PUBLICATIONS

Webster's New World Dictionary, 3rd College Ed. pp. 860, 873.

Primary Examiner—Edward J. Webman
Attorney, Agent, or Firm—Arthur W. Fisher, III

[57] ABSTRACT

A non-toxic hypocompatible biodegradable germicide effective against a wide range of pathogenic organisms comprising a composition including a monohydric alcohol from the group consisting of isopropyl, methyl, ethyl, n-propyl, n-butyl, tert-butyl or allyl or mixtures thereof and a polyhydric alcohol from the group consisting of propylene glycol; 1,3 propanediol; 1,2 butanediol, PEG 400; glycerol or 1,4 butanediol or mixtures thereof in proportion by weight such that the polyhydric alcohol reduces the surface glaze formed by the monohydric alcohol and surface tension formed by water or water-based body fluids enabling the disinfectant/antiseptic to kill the pathogenic organisms and act equally effective on a patient or inanimate surface without deleterious effect to either.

8 Claims, No Drawings

NON-TOXIC HYPOCOMPATIBLE BIODEGRADABLE GERMICIDE

This application is a continuation-in-part application of pending application Ser. No. 846,249 filed Feb. 24, 1992, abandoned; that is a continuation-in-part application of application Ser. No. 642,709, filed Jan. 17, 1991 and issued as U.S. Pat. No. 5,145,663 on Sep. 8, 1992; that is a continuation application Ser. No. 304,312 filed Jan. 31, 1989, now abandoned.

BACKGROUND OF THE INVENTION

1. Field of the Invention

A non-toxic hypocompatible biodegradable germicide effective against a wide range of pathogenic organisms.

2. Description of the Prior Art

Modern health care facilities are confronted with complex medical problems, whether in a practioner's office, clinic or large hospital. Such facilities must care for persons with life-threatening diseases while protecting other patients in the same facility from becoming infected. Thus, controlling viral and microbial contamination is a critically important task facing health care facilities today.

In the past, the health care industry believed that sanitation and disinfection applied primarily only to emergency rooms and operating rooms or suites. However, today health care provides an awareness that chemical sanitation and disinfection is necessary in virtually every area of the modern treatment facility.

This awareness has been heightened by the rapid increases in the spread of deadly communicable diseases such as the AIDS virus (HIV), hepatitis and tuberculosis, which has dramatically increased public awareness for the need of an effective protective means.

The need for such protective means applies equally to contaminated surfaces not only to health care facilities but to such environs as public restrooms, telephones, tables and other surfaces contacted by the public as well as for topical application directly on a patient's skin.

Various spray germicides for sanitizing such surfaces is typified by in U.S. Pat. No. 3,445,564. U.S. Pat. No. 3,445,564 is directed to a method, compositions and articles for sanitizing public or communal facilities prior to individual use. The method consists of applying a thin layer of a rapidly drying liquid germicidal composition to a surface such as a toilet seat. The rapidly drying germicidal compositions consist essentially of a lower aliphatic alcohol and at least about 5 percent of a volatizing agent therefor, such as acetone. Isopropyl alcohol has excellent germicidal activity and is sufficiently volatile to give a satisfactory drying rate when blended with suitable proportions of a volatilizing agent. Inasmuch as the lower aliphatic alcohols are not sufficiently volatile to afford usefully short drying times for practical purposes in the method and articles of the Kirschner invention it was necessary to include a volatilizing agent in the germicidal composition.

The proportion of volatizing agent to lower aliphatic alcohol in the rapidly drying germicidal compositions employed in the invention may vary widely depending upon a number of factors, which include among others, the volatility of the alcohol employed, the volatility of the volatilizing agent, the desired drying rate of the germicidal composition, the amount of germicidal agent applied to the surface to be treated and the method of application of the germicide, not to mention the prevailing conditions of temperature and relative humidity under which the product is to be employed.

Although the isopropyl alcohol-acetone composition of U.S. Pat. No. 3,445,564 has germicidal activity against bacteria, fungi and other lower organisms, additional antibacterial, antifungal or other active ingredients may be incorporated to enhance the overall germicidal effectiveness. Suitable germicidal additives include the well known antibacterial quaternary ammonium compound. In essence, U.S. Pat. No. 3,445,564 teaches the use of isopropyl alcohol to kill a limited number of germs on a dry toilet seat with the addition of acetone to volatize an already highly volatile chemical to rapidly dry the toilet seat for use within 30 seconds.

The use of a dye in a bactericidal solution as disclosed in U.S. Pat. No. 2,449,274 is employed to provide a visual indication of the effectiveness of such sprays.

U.S. Pat. No. 4,678,658 shows an aerosol spray for use in disinfecting a surface for personal use such as a public restroom facility or telephone. The composition and delivery of the compositions provides for the placement of a spray of disinfectant which includes a dye that disappears as the spray effects the germicidal activity of the disinfectant. The composition is also rapidly drying, so that the dye disappears as well as the disinfecting composition leaving the surface dry. However, the spray is corrosive and environmentally unsafe.

U.S. Pat. No. 3,821,413 discloses a formulation of materials which permits an effective, uniform rate of evaporation of glycols from an air circulator device to reduce airborne bacteria in the surrounding atmosphere. It was observed that the relative amounts and identities of the components of the invention are critical to the attainment of the desired continuous evaporation of glycols over a prolonged period of time.

The composition of U.S. Pat. No. 3,821,413 is a single phase liquid composition especially adapted for volatilization at a substantially uniform rate from the air circulator device. Generally speaking, the composition includes three essential components (1) a glycol, (2) an organic polar coupling compound for maintaining the homogeneity prevents the glycol from separating from the mixture during evaporation of the mixture into the atmosphere and (3) an organic, relatively non-polar compound for forming hydrophobic micelles with the glycol molecules in the resulting mixture for reducing the affinity of the glycol to atmospheric moisture and thereby increasing the rate at which the glycol may be evaporated into the atmosphere.

The composition contains the glycol germicide. If desired, other suitable germicides or antiseptic agents can be added provided, however, that the glycol concentration of the composition does not fall below 5 percent by weight of the total mixture. Such germicides include quaternary ammonium compounds, phanols, bisphenols, salicylanilides, carbanilides, formaldehyde and chloride.

The required glycol evaporation rate for attaining the desired air sanitizing performance depends on the satisfactory stability and uniform nature of the liquid composition during evaporation from the mixture. Accordingly, the compositions of the invention include from about 2 percent to about 40 percent by weight of an organic polar coupling compound for maintaining the homogeneity of the mixture to prevent the glycol from separating from the mixture during the evaporation process.

The affinity of glycols to attract atmospheric moisture significantly reduces their volatility and impairs their evaporation rate. Accordingly, the compositions of the invention include from about 5 percent to about 80 percent by weight of an organic, relatively non-polar compound for forming hydrophobic micelles surrounding the glycol molecules in the mixture for reducing the affinity of the glycol to atmospheric moisture and thereby increase the rate of evaporation of the glycol. Without this micelle formation, it was found that the glycol or mixture of glycols in the mixture cannot evaporate appreciably in an air circulator device containing a wick immersed in the liquid composition.

U.S. Pat. No. 3,806,593 is directed to an acne treatment medication applied to the skin for preventing the formation of acne or decreasing already established acne. An important factor for the occurrence of ache is the presence of bacteria in the sebaceous glands in the skin. It is known that the bacteria in the sebaceous glands form esterases which hydrolyze the sebum fats to alcohols and free fatty acids.

The medicinal acne-preventing or acne-diminishing composition of U.S. Pat. No. 3,806,593 is based on the bacterial esterase activity in the sebaceous glands which together with the water already present in the skin can hydrolyze an ester having a good penetration capacity into the sebaceous glands to form one and preferably two antibacterially active components, viz. an acid and an alcohol, which are harmless to the skin. The active compound in the composition is one or more esters chosen from the group consisting of ethyl lactate, isopropyl lactate and/or glycerol mono or dilactate. The esters hydrolyze in the sebaceous glands due to the esterases present in the glands to form the corresponding acids and alcohols. Lactic acid and the lower alcohols and also glycerol to a certain extent exert a good antibacterial activity when formed in situ in the sebaceous glands. The esters are lipophilic and can thus penetrate into the said glands. Even if a beneficial action can be achieved by application of the ester or esters per se it has been found to be suitable to apply the ester in the form of a solution in ethyl alcohol or isopropyl alcohol. The alcohol prevents hydrolysis of the ester already in the composition. the alcohol moves the hydrolysis equilibrium towards ester formation. The alcohol can also facilitate the penetration of the ester into the skin.

As is well-known alcohol in high concentrations may cause a drying-out of the skin. To counteract this effect, the composition may include a moisture-retaining agent such as a lower, suitably water-free polyol, viz. propylene glycol or glycerol. The content of propylene glycol or glycerol in the composition according to the invention may be up to 25 percent, suitably not more than 10 percent by weight and preferably 1–5 percent. High levels of polyol tend to make the composition smeary upon application on the skin and should thus be avoided.

The preferred composition according to the invention consists of about 15 percent by weight of ethyl lactate, about 2 percent by weight of propylene glycol, the remainder being ethyl alcohol.

In summary, U.S. Pat. No. 3,806,593 relates to acne medication comprising esters that hydrolize in the sebaceous glands in combination with an alcohol to prevent hydrolysis of the esters as well facilitate the penetration of the ester into the skin, and propylene glycol or glycerol to prevent drying of the skin. The preferred ratio of the constituents is 15 percent to 83 percent to 2 percent respectively.

U.S. Pat. No. 4,664,909 discloses a stable, fast drying pituitous powder deodorant suspension in an alcohol media containing a minimal amount of water and a critical amount of the essential hydroxyethyl cellulose as the suspending agent.

The fast drying pituitous suspension of particulate material in an aqueous alcohol media contains hydroxyethyl cellulose at levels above its normal solubility limit by polyhydric alcohol.

More specifically, U.S. Pat. No. 4,664,909 relates to stable pituitous suspensions of particulate material, preferably about 1–20 percent, uniformly suspended in alcohol/aqueous media containing a high alcohol content and a lower water content. The alcohol media may be a lower monohydric alcohol selected from the group consisting of methanol, ethanol, isopropanol and mixtures thereof. The use of polyhydric alcohols such as propylene glycol, butylene glycol and polyols thereof, and glycerin decreases the critical water level required in the hydroxyethyl cellulose-containing alcohol media.

It has been unexpectedly found that powders can be suspended in alcoholic/aqueous media containing a high alcohol content and a lower water content by using the water soluble polymer hydroxyethyl cellulose at critical levels above its ethanol solubility range which may be broadened by specified polyhydric alcohols. This polymer is unique in its property to form stable suspensions.

Specifically, polyhydric alcohols can be partially substituted for the monohydric alcohol, not to exceed the monohydric alcohol content. The monohydric alcohol content, such as ethanol, must exceed the upper solubility level for the water soluble polymer hydroxyethyl cellulose in ethanol or other lower alkanol. The reported upper solubility level of this water soluble polymer in ethanol is 70 percent. Below this level and within normal soluble use ranges, a uniformly viscous liquid is obtained which pours evenly. Although, it appears aesthetically desirable, it will not support suspended powder and segregation occurs. However, at ethanol concentrations above its solubility range, the polymer becomes less soluble and forms the desired pititious type liquid. If ethanol is further increased resulting in very low water levels the polymer will precipitate out and its suspending properties are again lost. Accordingly, a 70:30 ratio of ethanol-water is optimum. However, it was found that this problem can be eliminated by the sufficient addition of a polyhydric alcohol such as glycerine, propylene glycol, butylene glycol and polyglycols thereto.

Accordingly, it has been found that the monohydric alcohol constitutes about 55–85 percent; and the water content may be as low as 5 percent if at least 10 percent polyhydric alcohol is also present in the suspension. The combined water and polyhydric alcohol content is at least 15 percent and may be up to about 25 percent. Thus, it is apparent that the proportions of monohydric alcohol, water and polyhydric alcohol are interdependent.

In summary, U.S. Pat. No. 4,664,909 teaches a fast-drying deodorant comprising a critical amount of hydroxyethyl cellose as the deodorant to encapsulate or isolate bacteria to prevent growth of the bacteria, suspended in a solution of monohydric alcohol to provide the fast drying characteristics and polyhydric alcohol to improve the overall soluability of the solution to allow the use of increased levels of monohydric alcohol. The relative proportions of the monohydric alcohol, water and polyhydric alcohol are driven or determined by the desired solubility and therefore are interdependent.

U.S. Pat. No. 3,966,902 disclosed various polymer complex carriers such as propylene glycol for use with an active ingredient such as a disinfectant or fragrance.

U.S. Pat. No. 4,690,779 refers to the use of propylene glycol in combination with alcohol and fragrances. This composition is both toxic and non-biodegradable.

U.S. Pat. No. 4,209,500 teaches a composition suitable for use in aerosol sprays including an anhydrous alcohol and fragrance or perfume. This composition is corrosive, non-biodegradable and non-evaporative.

Additional examples of the prior art are found in U.S. Pat. No. 580,213, 4,282,179, 4,265,899, 4,283,421, 4,364,515, 4,550,105, 4,105,431, 4,243,403, 4,278,206, 4,322,475, 4,436,732, 4,597,887, 4,252,694, 4,279,762, 4,325,201, 4,540,505 and 4,675,397.

Examination of the prior art reveals that most existing disinfectants are either toxic or non-biodegradable or both. Toxic chemicals that are not biodegradable contaminate the environment, the soil and the water supply. Recent federal, state and local regulations are designed to reduce or eliminate such environmental contamination resulting from the use of such disinfectants.

In recognition of the dangers of existing disinfectants, health facilities are required to notify employees that toxic chemicals are in use and inform them of the possible hazards that result or could result as a consequence of misuse or spills. Such notices must also be given to the community at large.

Other laws and regulations require users to document the use of toxic chemicals and require that the excess, waste and residue be collected and properly stored. These materials must be collected by licensed and approved toxic waste companies, taken to authorized disposal sites and legally destroyed. The cost of disposing of such toxic material is often more expensive than the initial purchase price.

Simply stated, the prior art fails to teach or suggest an effective non-toxic biodegradable surface active disinfectant/antiseptic for application on contaminated surfaces or for safe use on a patient's skin.

Disinfectants today should be non-toxic as well as biodegradable, capable of killing or inactivating pathogenic organisms. Further, such disinfectants should be chemically compatible with the numerous different surfaces found in modern healthcare facilities.

As described more fully hereinafter the instant invention is directed to an environmentally safe germicide capable of killing anaerobic and aerobic bacteria, viruses including the HIV virus, mildew, mold and fungus. The principal active anti-microbial, anti-viral ingredients of the instant invention are selected from a group of monohydric alcohols and polyhydric alcohols.

In the past such alcohols have had limited use outside the laboratory due to various undesirable characteristics of alcohol. For example, it has been universally accepted that alcohol has very limited application as a widely used disinfectant because alcohol is unable to penetrate protein rich material, evaporates quickly, has limited stability and shelf life, has a pungent odor, tends to form a glaze on hard surfaces possibly hiding or covering visible contamination and dries the skin.

The instant invention has involved an extensive development program involving the unexpected formulation of certain chemicals to reduce or inhibit those undesirable features of alcohol and to make alcohol safe and effective for use outside the laboratory.

SUMMARY OF THE INVENTION

The present invention relates to a non-toxic hypocompatible biodegradable germicide for topical application on a patient's skin or to inanimate surfaces to kill a wide range of pathogenic organisms.

The biodegradable germicide comprises a composition including a monohydric alcohol from the group consisting of isopropyl, methyl, ethyl, n-propyl, n-butyl, tert-butyl alcohol or allyl alcohol and/or mixtures thereof and a polyhydric alcohol from the group consisting of propylene glycol; 1,3 propanediol; 1,2 butanediol, PEG 400; glycerol or 1,4 butanediol and/or mixtures thereof in proportion by weight such that the polyhydric alcohol reduces the surface glaze formed by the monohydric alcohol and surface tension formed by water or water-based body fluids enabling the germicide to kill the pathogenic organisms and act equally effective on a patient or inanimate surface without deleterious effect to either.

The monohydric alcohol provides the primary disinfecting or killing effect on the pathogenic organisms; while, the polyhydric alcohol lowers the flash point of the composition and soothes the skin. The polyhydric alcohol also slows the rate of evaporation, reduces or eliminates the intersurface glazing effect of monohydric alcohol and homogenizes the interactive ingredients.

The relative proportions by weight of interactive ingredients chemically reduces the tensile strength of the surface liquids on the patient's skin or other surface permitting the germicidal effect to act directly on the pathogenic organisms.

The non-toxic hypocompatible biodegradable germicide in liquid form may be dispensed in various delivery systems including spray, foam, pour and squirt for a aerosol or non-aerosol product. Alternate systems may include a towelette or an absorbent wipe containing the product in an airtight enveloping material such as sealed foil or other wrapping material could be used for a single application.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

Numerous germicidal compositions and delivery devices have been developed to kill various pathogenic organisms. The wide range of application or use is limited by the chemical and biological effect of such compositions on the various surfaces, delivery means and patients exposed to such germicidal compositions.

The present invention relates to a non-toxic hypocompatible biodegradable germicide for topical application on a patient's skin or on hard surfaces such as restrooms or tables effective against a wide range of target pathogenic organisms such as bacteria including *Staphylococcus aureus, Pseudomonas aeruginosa* and *Salmonella choleraesuis*, HIV I, HIV-II, Tuberculosis, polio, Herpes simplex type 2, as well as fungi *Trichophyton mentagrophytus*, mold and mildew through alternate delivery means.

The germicide comprises a non-toxic hypocompatible biodegradable composition of selected monohydric alcohols, selected polyhydric alcohols and water combined in relative proportions by weight such that the composition may be used topically to cleanse a patient's skin or to disinfect various public surfaces through direct application with equal effectiveness without deleterious effect to either.

The monohydric alcohol is selected from the group consisting of isopropyl, methyl, ethyl, n-propyl, n-butyl, tert-butyl or allyl or mixtures thereof and the polyhydric alcohol is selected from the group consisting of propylene glycol; 1,3 propanediol; 1,2 butanediol, PEG 400; glycerol or 1,4 butanediol or mixtures thereof.

As used herein, the term non-toxic refers to the requirements of the LD 50 Oral Toxicity Test; that is, non-toxic, non-poison, to rate at 50 times the lethal dose.

As used herein, the term biodegradable refers to decomposition in the presence of 25 percent organic material within 90 days at 69 degrees F. (Standard Temperature) with moisture content of 100 parts per million.

As used herein, the term challenge refers to a test colony or specimens of 106 specified pathogenic organisms.

As used herein, the term azeotropic means a constant boiling liquid admixture of two or more substances, whose admixture behaves as a single substance, in that the vapor, produced by partial evaporation or distillation of the liquid has the same composition as the liquid, i.e., the admixture distills without substantial composition change. Constant boiling compositions, which are characterized as azeotropic, exhibit either a maximum or minimum boiling point, as compared with that of the nonazeotropic mixtures of the same substances.

As used herein, the term organic means the presence of less than about 10 percent by weight of free water within a solution.

As used herein, the term aqueous means the presence of more than about 10 percent by weight of free water within a solution.

The specific monohydric alcohols and polyhydric alcohols and relative ratios thereof optimize the particular characteristics of solubility, specific gravity, conductivity, pH, flash point, boiling point and evaporation essential to the effective use of the instant germicide against the bioburden as defined herein on pathogens as described herein with a nontoxic effect as defined herein on patients, and with a hypocompatible effect as defined herein on the surfaces described herein.

Specifically, the presence of the polyhydric alcohol raises the boiling point of the germicide slowing the rate of evaporation of the germicide. As a solvent, the polyhydric alcohol prevents the tendency of monohydric alcohol to form a glaze on the target surface that masks the pathogenic organisms and breaks the barrier formed by surface tension of water and water-based body fluids enabling the germicide to act on the pathogens more rapidly. In addition, the polyhydric alcohol serves as an emulsifier to assure that the composition remains homogenized during storage and use.

Further, the polyhydric alcohol reduces the harmful effects of monohydric alcohol if swallowed or sprayed into the eyes or on mucus membranes as well as soothing the skin upon contact. Since the polyhydric alcohol reduces toxicity to human cells the need to dilute the germicide has been eliminated. Polyhydric alcohol also acts as a secondary disinfectant useful to disinfect air. In the preferred percentage used, tests indicate that the polyhydric alcohol increases the overall effectiveness of the germicide against most viruses, mold and mildew.

Since the germicide was developed for use on a wide variety of surfaces and dispensed from a number of dispensing modes or means of dispersant materials the measure of chemical resistance is important to permit broad use and application. To be effective, the germicide must be hypocompatable with CPVC, Epoxy, Polypropylene, PVC, Cyolac (ABS), Phenolic, Nylon, Noryl, Delrin (Acetal), Ryton to 200%F, Kynar, Teflon, Stainless Steel 316, Stainless Steel 304, Carpenter 20, Stainless steel (440), Titanium, Cast Bronze, Cast Iron, Aluminum, Hastelloy C, Carbon/ceramic, Ceramagnet A, Viton, Buna N., Neoprene, Nitrile, Natural rubber, Hypalon, EPDM, Kel-F, Tygon, Silicone, Ceramic and Carbon/graphite.

As used herein, the term hypocompatible shall mean no material degradation efforts associated with surfaces to include, for example, discoloration, corrosion, cracking, crazing and embrittlement.

Comparative results of the germicide with the individual constituents have demonstrated that the combination of interactive ingredients provides a germicide effective against an expansive range of materials found in a wide variety environments through various delivery means such as aerosol, pump, spray or swab without degradation of the materials.

In order to accomplish the design criteria of a nontoxic, hypocompatible, biodegradable germicide effective against the wide range of pathogenic organisms described herein, the composition should have a pH of between about 7 and 5, virtually evaporate before about 6 and 20 minutes to have an effective kill time of about 8 to 12 minutes and prevent surface residue, a specific gravity of about 0.85, viscosity below 4 and relatively no conductivity.

The effective proportional relationship of the ingredients by weight for the monohydric alcohol as described herein is between about 65 percent to about 75 percent, for the polyhydric alcohol as described herein is between about 4 percent and about 16 percent and for the water is between about 9 percent to about 18 percent.

The preferred proportional relationship of the active ingredients by weight is about 70 percent for the monohydric alcohol and between about 8 percent to about 12 percent for the polyhydric alcohol and between about 14 percent to about 18 percent water. The preferable amount of polyhydric alcohol is 6 to 14 percent by weight. Less than 4 percent of polyhydric alcohol by weight does not provide adequate kill and exhibits an excessive alkaline pH; while, more than 16 percent of polyhydric alcohol by weight leaves a residue to attract and harbor pathogens. However, the composition is most effective with about 10 percent polyhydric alcohol, about 70 percent monohydric alcohol, and about 16 percent water all by weight.

The solution comprises a binary azeotropic composition formed by the chemical bonding between the monohydric alcohol and water in correct proportion to lengthen shelf life, reduce evaporation and rust, and enhance efficacy. Specifically, because the azeotrope is stable, the composition will maintain the efficacy for long periods of time. The azeotropic bond between the monohydric alcohol and water causes the combination to evaporate together thus maintaining substantially the same relative concentration of monohydric alcohol and water to retain sufficient potency to kill the target organisms. Moreover, because the water is bonded to the monohydric alcohol, the ability to oxidize metal (rust) is greatly reduced. Thus, after registering significant amounts of evaporation in laboratory tests, presumed loss of efficacy would be expected. Because of the azeotrope however, even after a 33 percent weight loss, the concentration of monohydric alcohol was still at 66 percent. Therefore, most of the evaporation was from the free water plus some of the azeotropic monohydric alcohol. Regardless of extended shelf life, exposure to air in an ultrasound, or carelessness with regard to keeping containers tightly sealed, the required concentration of monohydric alcohol essential to achieve accepted and required testing protocols will be maintained.

In the total concentrations used in the solution about 70 percent monohydric alcohol requires about 10 percent water to be azeotropic. An additional amount of water up to 10 percent may be added to the composition for a total of 20 percent of water by weight without destroying the azeotropic conditions of the monohydric alcohol or diminishing the disinfectant capability of the composition against hydrophobic organisms.

The addition of between about 2 percent and 4 percent by weight of a surfactant such as sodium dodecyl sulfate, octyl phenoxy polyethoxyethanol, triethanol amine lauryl sulfate and mixtures thereof permits the use of the composition as a surface disinfectant capable of dislodging and absorbing as much as twenty five percent organic matter from an inanimate surface.

The addition of between about 1 percent and 2 percent by weight of a sporicide such as an N(hydroxymethyl) acetamide derivative permits the use of the composition as a sterilant capable of killing *Bacillus subtilis* and *Clostridium sparogenes.*

By adding a resin such as Carbopol 940 brand carboxy polymethylene by BF Goodrich from about 0.1 percent to 2.0 percent by weight to increase viscosity, the composition may be used as a commercial or industrial disinfecting lubricant.

It will thus be seen that the objects set forth above, among those made apparent from the preceding description are efficiently attained and since certain changes may be made in the above construction without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A non-toxic, hypocompatible, biodegradable germicide effective for contact and killing of a challenge of pathogenic organisms comprising *Staphylococcus aureus, Pseudomonas aeruginosa, Salmonella choleraesuis,* HIV I, HIV-II, tuberculosis, polio, herpes simplex type 2, *Trichophyton mentagrophytes* or mold, said germicide comprising;
   (i) a disinfecting amount of at least about 65% to about 75% by weight of at least one monohydric alcohol selected from the group consisting of isopropyl, methyl, ethyl, n-propyl, n-butyl, tert-butyl, allyl alcohols and mixtures thereof;
   (ii) a surface glaze reducing amount of from about 4% to about 16% by weight of at least one polyhydric alcohol, selected from the group consisting of isopropyl, methyl, ethyl, n-propyl, n-butyl, tert-butyl, allyl alcohols, and mixtures thereof;
   (iii) from at least about 9% to about 20% by weight water in an organic azeotropic combination with the monohydric alcohol; and
   wherein components (i), (ii) and (iii) are mixed homogeneously with a pH of from about 5 to about 7 and in proportions effective to interact in a manner to reduce surface glaze formed on pathogenic organisms to be disinfected and reduce the surface tension of water or water-based body fluids containing the pathogenic organisms found on a surface to be disinfected, such that the pathogenic organisms of said challenge can be contacted and killed before evaporation of said monohydric alcohol.

2. A germicide according to claim 1, comprising about 70 percent by weight monohydric alcohol.

3. A germicide according to claim 2, comprising about 8 to 12 percent by weight polyhydric alcohol.

4. A germicide according to claim 3, comprising about 10 percent by weight of said polyhydric alcohol.

5. A germicide according to claim 4, comprising about 16 percent by weight water.

6. A germicide according to claim 1, comprising at least about 16 percent by weight water.

7. A germicide according to claim 1, effective against a $10^6$ challenge of *Staphylococcus aureus, Pseudomonas aeruginosa, Salmonella choleraesuis,* HIV-I, HIV-II, tuberculosis, polio, herpes simplex type 2, *Trichophyton metagrophytes,* mold or mildew.

8. A germicide according to claim 7, having an effective kill time for said challenge of from about 8 to 12 minutes.

* * * * *

UNITED STATES PATENT AND TRADEMARK OFFICE
CERTIFICATE OF CORRECTION

| | |
|---|---|
| PATENT NO. | : 5,441,723 |
| APPLICATION NO. | : 08/092556 |
| DATED | : August 15, 1995 |
| INVENTOR(S) | : Paul L. Simmons |

It is certified that error appears in the above-identified patent and that said Letters Patent is hereby corrected as shown below:

Column 10, Lines 14 through 18 should read as follows:

(ii) a surface glaze reducing amount of from about 4% to about 16% by weight of at least one polyhydric alcohol, selected from the group consisting of propylene glycol, 1,3 propanediol, 1,2 butanediol, polyethylene glycol, glycol, 1,4 butanediol, and mixtures thereof.

Signed and Sealed this

Eighteenth Day of July, 2006

JON W. DUDAS
*Director of the United States Patent and Trademark Office*